United States Patent
Goodfellow et al.

(10) Patent No.: US 10,376,370 B2
(45) Date of Patent: Aug. 13, 2019

(54) UNICONDYLAR MENISCAL BEARING KNEE REPLACEMENT

(75) Inventors: John William Goodfellow, Oxfordshire (GB); Colin Hunsley, legal representative, Hants (GB); John O'Connor, Oxfordshire (GB); Chris Alexander Dodd, Oxfordshire (GB); David Wycliffe Murray, Oxfordshire (GB)

(73) Assignees: John Joseph O'Connor, Oxford (GB); David Wycliffe Murray, Oxford (GB); John Goodfellow, Oxford (GB); Chris Dodd, Oxford (GB); Biomet UK Limited, Bridgend, South Glamorgan (GB)

( * ) Notice: Subject to any disclaimer, the term of this patent is extended or adjusted under 35 U.S.C. 154(b) by 575 days.

(21) Appl. No.: 13/821,453

(22) PCT Filed: Aug. 31, 2011

(86) PCT No.: PCT/GB2011/051633
§ 371 (c)(1),
(2), (4) Date: Jun. 18, 2013

(87) PCT Pub. No.: WO2012/032329
PCT Pub. Date: Mar. 15, 2012

(65) Prior Publication Data
US 2013/0274888 A1    Oct. 17, 2013

Related U.S. Application Data (60) Provisional application No. 61/382,163, filed on Sep. 13, 2010.

(30) Foreign Application Priority Data

Sep. 7, 2010 (GB) .................................. 1014824.5

(51) Int. Cl.
*A61F 2/38* (2006.01)
*A61F 2/30* (2006.01)

(52) U.S. Cl.
CPC .............. *A61F 2/38* (2013.01); *A61F 2/3868* (2013.01); *A61F 2002/30616* (2013.01); *A61F 2002/3895* (2013.01)

(58) Field of Classification Search
CPC ... A61F 2/38; A61F 2/3868; A61F 2002/3895
See application file for complete search history.

(56) References Cited

U.S. PATENT DOCUMENTS

| | | |
|---|---|---|
| 4,880,429 A | 11/1989 | Stone |
| 5,871,542 A | 2/1999 | Goodfellow et al. |
| (Continued) | | |

FOREIGN PATENT DOCUMENTS

| | | |
|---|---|---|
| EP | 1 543 802 A2 | 6/2005 |
| EP | 2613740 B1 | 8/2016 |
| (Continued) | | |

OTHER PUBLICATIONS

Notification of Transmittal of the International Search Report and the Written Opinion of the international Searching Authority dated Dec. 15, 2011 in connection with International Patent Application No. PCT/GB2011/051633.

(Continued)

*Primary Examiner* — Bruce E Snow
(74) *Attorney, Agent, or Firm* — Schwegman Lundberg & Woessner, P.A.

(57) ABSTRACT

A kit of parts for use in unicondylar meniscal bearing knee replacement comprises a plurality of meniscal bearings, each meniscal bearing comprising a body defining a dished first bearing surface on one side thereof and a second surface on an opposing side of the body. Each meniscal bearing has an entrapment between 3.2 mm and 3.8 mm. Meniscal (Continued)

bearings and methods of performing unicondylar meniscal bearing replacements are also described.

17 Claims, 7 Drawing Sheets (56) References Cited

U.S. PATENT DOCUMENTS

| | | |
|---|---|---|
| 6,206,927 B1 | 3/2001 | Fell et al. |
| 2006/0036329 A1 | 2/2006 | Webster et al. |
| 2006/0111726 A1 | 5/2006 | Felt et al. |
| 2006/0190086 A1 | 8/2006 | Clemow et al. |
| 2009/0259314 A1 | 10/2009 | Linder-Ganz et al. |

FOREIGN PATENT DOCUMENTS

| | | |
|---|---|---|
| FR | 2836821 A | 9/2003 |
| GB | 1534263 A | 11/1978 |
| WO | WO 00/59411 A1 | 10/2000 |
| WO | WO 2004/006811 A2 | 1/2004 |
| WO | WO 2004/069089 A2 | 8/2004 |
| WO | WO 2005/016175 A2 | 2/2005 |
| WO | WO 2008/045807 A2 | 4/2008 |
| WO | WO 2009/154847 A2 | 12/2009 |
| WO | WO-2010032329 A1 | 3/2010 |
| WO | WO-2012032329 A1 | 3/2012 |

OTHER PUBLICATIONS

Search Report dated Nov. 17, 2010 in connection with United Kingdom Patent Application No. GB1014824.5.
Notification of First Office Action dated Jan. 27, 2015 in connection with Chinese Patent Application No. 201180049773.3; 16 pages.
"Chinese Application No. 201180049773.3, Office Action dated Sep. 1, 2015", (W/ English Translation), 12 pgs.
"International Application Serial No. PCT/GB2011/051633, International Preliminary Report on Patentability dated Mar. 21, 2013", 9 pgs.
"International Application Serial No. PCT/GB2011/051633, International Search Report dated Dec. 15, 2011", 5 pgs.
"International Application Serial No. PCT/GB2011/051633, Written Opinion dated Dec. 15, 2011", 7 pgs.
"Chinese Application Serial No. 201180049773.3, Office Action dated Feb. 15, 2016", (W/English Translation), 6 pgs.
"European Application Serial No. 11760533.7, Office Action dated May 13, 2013", 2 pgs.
"European Application Serial No. 11760533.7, Response filed Nov. 12, 2013 to Office Action dated May 13, 2013", 13 pgs.
"Chinese Application Serial No. 201180049773.3, Office Action dated Sep. 1, 2015", 12 pgs.

Fig. 8

UNICONDYLAR MENISCAL BEARING KNEE REPLACEMENT

CROSS-REFERENCE TO RELATED APPLICATION(S)

The present application claims priority under 35 U.S.C. § 365 to International Patent Application No. PCT/GB2011/051633 filed Aug. 31, 2011. International Patent Application No. PCT/GB2011/051633 claims priority under 35 U.S.C. § 365 and/or 35 U.S.C. § 119(a) to United Kingdom Patent Application No. 1014824.5 filed Sep. 7, 2010 and U.S. Provisional Patent Application No. 61/382,163 filed Sep. 13, 2010 which are incorporated herein by reference into the present disclosure as if fully set forth herein.

FIELD OF THE INVENTION

The present invention relates to a kit of parts for use in unicondylar meniscal bearing knee replacement, a meniscal bearing for use in unicondylar meniscal bearing knee replacement and a method of performing unicondylar meniscal bearing knee replacement.

BACKGROUND OF THE INVENTION

The knee comprises three inter-dependent joints in three separate compartments, all surrounded by a fibrous capsule covered by the skin. The medial tibio-femoral joint involves contact between the thigh bone (the femur) and the leg bone (the tibia) on the inside of the lower limb. The lateral tibio-femoral joint involves contact between the femur and the tibia on the outside of the lower limb. The patello-femoral joint involves contact between the femur and the knee cap (the patella) on the front of the lower limb.

The front of the lower (distal) end of the femur comprises an anticlastic flanged groove, convex in the sagittal plane, transversely concave, providing a track for the patella. The back of the distal femur divides into two separate near-spherical convex condyles making contact with the tibia. The upper surface of the tibia is like a plateau which is slightly dished on the medial side for contact with the medial femoral condyle forming the medial tibio-femoral joint and slightly convex on the lateral side for contact with the lateral femoral condyle forming the lateral tibio-femoral joint with a protrusion (the tibial eminence) running from front to back between the joints.

The articulating surfaces in each joint are covered with thin layers of a tough protective layer, called cartilage, and are lubricated by synovial fluid secreted from a membrane on the inner surface of the fibrous capsule surrounding the knee. The surfaces of the tibio-femoral joints are further separated by the menisci, semi-circular semi-lunar collagen bundles oriented circumferentially. Each bundle is securely attached at each end to the tibia and loosely to the peripheral capsule. The menisci form closely-fitting mobile sockets for the femoral condyles bringing the dissimilar surfaces of the femur and tibia into closer conformity while allowing some antero-posterior translation of the femoral condyles on the tibia.

The bones are held together actively by muscles with their tendons which span the joints and passively by ligaments and the joint capsule. The ligaments comprise bundles of collagen fibres running mainly longitudinally. The collateral ligaments arise on the external surfaces of the medial and lateral condyles. The medial collateral ligament inserts into the external medial surface of the proximal tibia. The lateral collateral ligament inserts into the proximal surface of the fibula. The medial collateral ligament is a much larger and stiffer structure than the lateral collateral ligament. The cruciate ligaments arise from the internal surfaces of the femoral condyles and insert into the tibial eminence.

The ligaments and the bones together form a mechanism which controls a complex pattern of movement of the bones on each other. In the unloaded state, flexion of the knee to 130° about a transverse axis is accompanied by approximately 25° rotation about the axis of the tibia (axial rotation). These movements are accommodated by mainly antero-posterior translations of the tibio-femoral contact areas so that the bones roll as well as slide on each other and the patella slides over the anterior femur. Additionally, the femoral condyles can spin about the axis f the tibia. The joint also allows approximately 5° of rotation about an antero-posterior axis (abduction-adduction). Under load, the ligaments stretch and the articular surfaces indent, significantly modifying the relationship between flexion, axial rotation and abduction-adduction and between flexion and contact area translations. Movements at the knee are therefore load- and activity-dependent.

Damage to the articular surfaces or to the ligaments changes the patterns of movement of the bones on each other and the response of the joint to load. Osteoarthritis follows from failure of the cartilage in one or other of the three joints, leading to bone-on-bone contact and the onset of pain. Frequently, osteoarthritis first manifests itself in the medial compartment, while the ligaments remain intact. The disease can remain confined to the medial compartment until the anterior cruciate ligament fails and the disease then spreads to the other two compartments. No drug based treatment has been found which halts or reverses these processes.

Total knee replacement is the most common surgical treatment for osteoarthritis, involving replacement of the articular surfaces of all three compartments and sacrifice of some of the ligaments. Partial knee replacement involves replacement of the articular surfaces in only one compartment, leaving intact the surfaces of the other two compartments and all of the ligaments. Partial knee replacement can act prophylactically, reducing the rate of development of the disease in the other compartments. Partial knee replacement is surgically more demanding and is therefore not always used when it is indicated.

To implant the prosthetic components of a knee replacement, sufficient sections of bone have to be removed from the surfaces of the tibia and the femur. The component parts of the prosthesis are then fitted accurately replacing the material removed by the surgeon.

Mobile bearing arthroplasty uses metal components fixed to the tibia and the femur with an intervening plastic bearing, an analogue of the natural meniscus, interposed therebetween. The bearing provides a mobile socket to bring the femoral component into conformity with the tibial component. The bearing has a concave socket on its upper surface for contact with the femoral component and a flatter lower surface for contact with the tibial component. The metal components are fixed to the bones so as to leave a constant minimum gap between them when the knee is flexed and extended. The most appropriate thickness of bearing is then chosen to fill that gap.

On implantation, the bearing is pushed between the metal femoral and tibial components against the resistance of stretching ligaments. This requires the thickest part of the posterior portion of the bearing to fit through the minimum gap between the round femoral component and the flatter tibial component. The ligament stretch required is the difference between the maximum thickness of the posterior end of the bearing and the minimum thickness of the bearing. This difference is known as the entrapment of the bearing.

In one version of the prior art, there are five sizes of bearing, from extra small to extra large, with dimensions other than thickness which vary parametrically with the radius of the spherical surface of the femoral component. The entrapment varies from about 3 mm in the extra-small to about 4 mm in the extra-large. The range of sizes is necessary to fit both small patients and large patients.

A complication of mobile bearing arthroplasty can be slack ligaments. As a result, the surgeon naturally seeks to use the thickest possible bearing to avoid slackness. Care has to be taken not to overstuff the joint, whereby a bearing that is too thick is selected. This leads to pain and failure of the components and, in the case of a partial knee replacement, degeneration of the preserved compartments.

It has been appreciated that post-operative pain is most commonly experienced after implantation of the smaller components. However, pain can also occur in larger bearings, as they require significant force for implantation, provided by the surgeon's thumbs.

It has been appreciated that some patients continue to have pain after a mobile bearing partial knee replacement. There is need for a bearing design with more entrapment for the smaller bearings and less entrapment for the larger bearings which may prevent overstuffing of the joint.

SUMMARY OF THE INVENTION

According to a first aspect the invention comprises a kit of parts for use in unicondylar meniscal bearing knee replacement, comprising a plurality of meniscal bearings, each meniscal bearing comprising a body defining a dished first bearing surface on one side thereof and a second surface on an opposing side of the body, in which each meniscal bearing has an entrapment, the entrapment of each meniscal bearing being between 3.2 mm and 3.8 mm.

Previously, it has been thought necessary to vary the entrapment dependent strongly upon the size of the patient and so the size of the medial bearing used. We have appreciated that, for smaller patients and bearings, prior art entrapments, which were generally smaller than the range discussed, did not sufficiently prevent dislocation of the knee joint. Furthermore, the relatively low entrapment meant that a surgeon could be tempted to implant a thicker bearing than is needed for very small patients. For larger patients and hence bearings, the reduction in entrapment from prior art bearings will make the bearing easier to fit.

Where the meniscal bearing has an anterior end and a posterior end, the entrapment may be defined as the difference in thickness between smaller of the maximum thicknesses between the first and second surfaces at the anterior and posterior end on the one part and the minimum thickness between the first and second surfaces on the other part.

The entrapment of the bearings may all be approximately the same, and may be 3.5 mm, with a typical tolerance of ±0.1 mm.

Each meniscal bearing may have a length from an anterior end to a posterior end. The meniscal bearings may have a plurality of different lengths, which may depend upon a radius of curvature of the first surface. The length of at least one of the meniscal bearings may be at least 39 mm, or at least 39.4 mm. Alternatively, the length of at least one of the meniscal bearings may be at least 36.8 mm. The length of at least one of the meniscal bearings may be less than 34.2 mm, 34 mm, 31.6 mm or 29.5 mm. Previously, kits of meniscal bearings would include at least one bearing of these sizes with an entrapment outside the range referred to above.

The meniscal bearings may have a plurality of different minimum thicknesses between the first and second surfaces. The meniscal bearings of a given length may have a plurality of different minimum thicknesses, but the same, or approximately the same, entrapment.

The kit may comprise meniscal bearings having a plurality, or all, of the lengths selected from the set comprising 29.2 mm (extra small), 31.6 mm (small), 34.2 mm (medium), 36.8 mm (large) and 39.5 mm (extra large). The tolerances on the measurements may be up to 0.5 mm. For each of the lengths of the set, there may be meniscal bearings having plurality, or all, of minimum thicknesses selected from the group comprising 7.0 mm, 8.0 mm, 9.0 mm, 10.0 mm and 11.0 mm. The tolerance of the thicknesses may be 0.25 mm.

As said before, the entrapment of all of these bearings will be in the range 3.2 mm to 3.8 mm, which is a considerable narrowing of the range of entrapments compared with prior art bearings. Compared to the prior art, the smaller bearings have an increased entrapment and the larger bearings have a decreased entrapment. For a smaller patient with a limited value of possible ligament stretch, the surgeon may be required to implant a thinner bearing compared to the prior art, resulting in slacker ligaments and less postoperative pain but without significantly increasing the risk of dislocation. In the larger patients with a limited value of ligament stretch, a bearing of the correct minimum thickness should be easier to implant compared to the prior art.

The meniscal bearings may be trial bearings for use in fitting a prosthesis, or implantable bearings for use with the prosthesis. The kit may comprise a set of trial bearings and a set of implantable bearings, each implantable bearing corresponding to a trial bearing.

The correspondence between trial and implantable bearings may be such that the surgeon fits the thickest grade trial bearing they can into the gap between the tibial and femoral components of a patient's knee, and then removes the trial bearing and selects the implantable bearing to be one grade thinner than the thickest trial bearing that fitted in the gap, and implants the selected bearing.

It will be appreciated that compared to the prior art, the smaller sets of implantable and trial bearings may have a greater entrapment and a thicker posterior end region (typically up to 0.5 mm thicker for the equivalent grade of a size range).

This should reduce the chance of dislocation of the bearing in use, and reduce the chance of overstuffing the joint by requiring the surgeon to choose a bearing of reduced minimum thickness compared to the prior art.

In some embodiments the meniscal bearings are symmetrical about either or both of a coronal and a sagittal plane; as such, they may be able to be inserted into the gap between the tibial and femoral prosthetic components either way around. This reduces the number of components required for manufacture, as the bearings will no longer be handed.

The kit may comprise at least one femoral prosthetic component having a spherical articular surface having a radius of curvature, the kit comprising meniscal bearings in which the first surface has the same radius of curvature. The kit may also comprise at least one tibial prosthetic component.

At least some embodiments of the present invention provide a bearing with a substantially conforming contact area between the articulating surfaces of the femoral component and the tibial component throughout extension and flexion. The bearing also provides an increase in and a substantially constant articulating contact surface area from extension through flexion which reduces overall stress and wear in the articulating contact area which provides femoral rollback relative to the tibial component.

Each meniscal bearing may comprise a protrusion at a posterior end thereof, an anterior thereof or both. This effectively increases a horizontal entrapment of the bearing.

Without a protrusion on the posterior end, the bearing could be easier to implant if it were slid around the femoral component rather than along the tibial component. This would increase the likelihood of overstuffing for a given entrapment. The posterior protrusion makes it more difficult to implant the bearing in this manner, thereby reducing the risk of overstuffing.

The protrusion may be semi-circular or any other convenient shape. The extent of the protrusion may be such so as not to press against the vital vessels passing across the back of the joint in use and can be designed to make implantation along the tibial component and the femoral component equally difficult.

A protrusion on the anterior surface of the bearing will decrease the likelihood of the bearing dislocating in the posterior direction. Likewise, a protrusion added to the posterior end of the bearing will decrease the likelihood of the bearing dislocating in the anterior direction.

The protrusion may be of even depth along the end to which it is added. Alternatively, the protrusion may have a reduced depth at the upper end of the surface compared with the lower end, giving a sloped edge. This may reduce the chance of the upper surface of the bearing coming into contact with the bone surrounding the femoral component.

According to a second aspect of the invention, there is provided a meniscal bearing for use in a unicondylar meniscal bearing knee replacement, comprising a body defining a dished first bearing surface on one side thereof and a second surface on an opposing side of the body, the meniscal bearing having a length from an anterior end to a posterior end being greater than 39 mm or less than 34.2 mm, and having an entrapment being the maximum difference in thickness between the first and second surfaces of between 3.2 mm and 3.8 mm. Preferably, the length is greater than 39.4 mm, or less than 34 mm or 31.6 mm.

The bearing may have any of the optional features discussed with respect to the meniscal bearing included in the kit of the first aspect of the invention.

According to third aspect of the invention, there is provided a method of performing a unicondylar meniscal bearing knee replacement, the method comprising the implantation of a femoral component into the femur of a patient, the implantation of a tibial component into the tibia of the patient, the selection of a meniscal bearing from the kit of the first aspect of the invention, or of a meniscal bearing according to the second aspect of the invention, and the insertion of the meniscal bearing between the femoral component and the tibial component.

In one embodiment, the method comprises inserting the bearing at an angle to an articular surface of tibial component so that the first surface of the meniscal bearing substantially contacts a bearing surface of the femoral component throughout insertion of the meniscal bearing. This may reduce the distraction of the femoral component that occurs during the implanting of the meniscal bearing compared to if the bearing is inserted with the second surface of the bearing substantially contacting the tibial tray. Reducing the distraction of the femoral component reduces the amount of ligament stretch required for implantation. For a given limit of ligament stretch and minimum bearing thickness, a bearing with a larger entrapment can be inserted into the gap without reaching the limit of ligament stretch, resulting in a better fitting bearing.

BRIEF DESCRIPTION OF DRAWINGS

The invention will now be described by way of example only, with reference to the accompanying drawings, of which.

DESCRIPTION OF EMBODIMENTS

Figure 1:
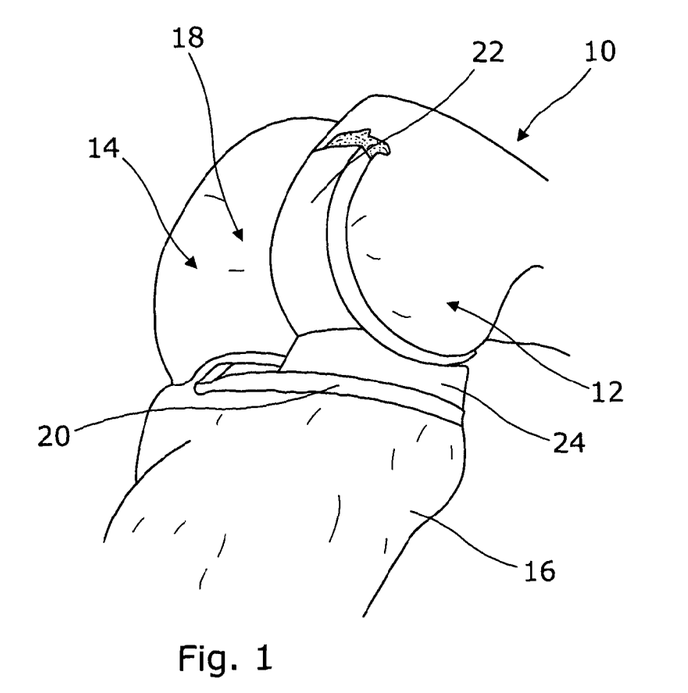
FIG. 1 shows a medial unicondylar arthroplasty.

FIG. 1 shows a right leg femur 10 having a medial condyle 12 and a lateral condyle 14, a tibia 16, and a medial unicondylar implant 18. The implant has three components: a metal tibial plate, or component, 20, a metal femoral component 22 and a plastics material (e.g. Ultra high Molecular weight polyethylene, UHMWPE) meniscal bearing 24. The materials named are those commonly used but they are not essential.

The bottom, second, surface of the meniscal bearing is flat or generally flat, whereas the upper, first, surface is a dished, concave, surface which surrounds the domed surface of the femoral component 22.

Figure 2A:
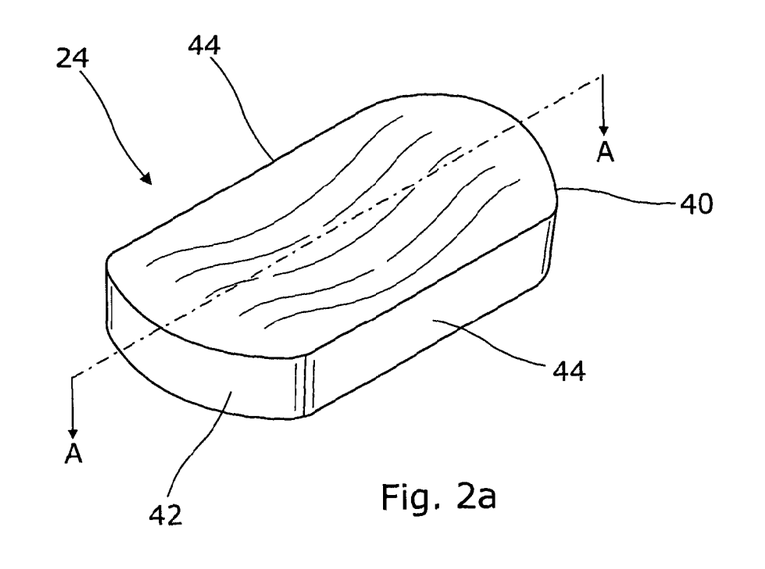
FIGS. 2a and 2b show schematically a meniscal bearing of the prosthesis of FIG. 1.
Figure 2B:
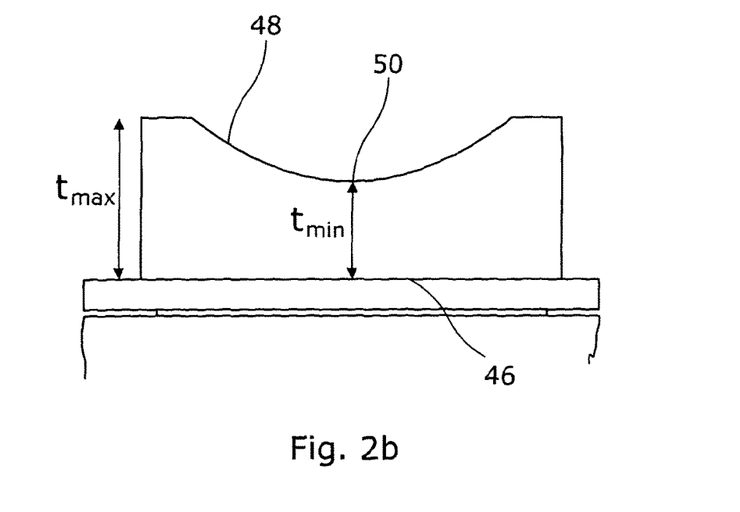

FIGS. 2a and 2b show schematically the meniscal bearing of FIG. 1. In this embodiment, the meniscal bearing 24 has a posterior end 40, an anterior end 42 and two generally parallel sides 44. The meniscal bearing 24 has a flat base 46 forming the second surface and a central dished upper portion 48 forming the first surface. The thickness of this bearing (reference $t_{max}$ in FIG. 2b) may not be the same at the anterior and posterior ends. The base surface 50 of the dished portion 48 is a distance $t_{min}$ above the flat base 46. The surface of the dished portion is generally part of a spherical surface. The entrapment of the bearing is $t_{max}$-$t_{min}$.

Figure 2C:
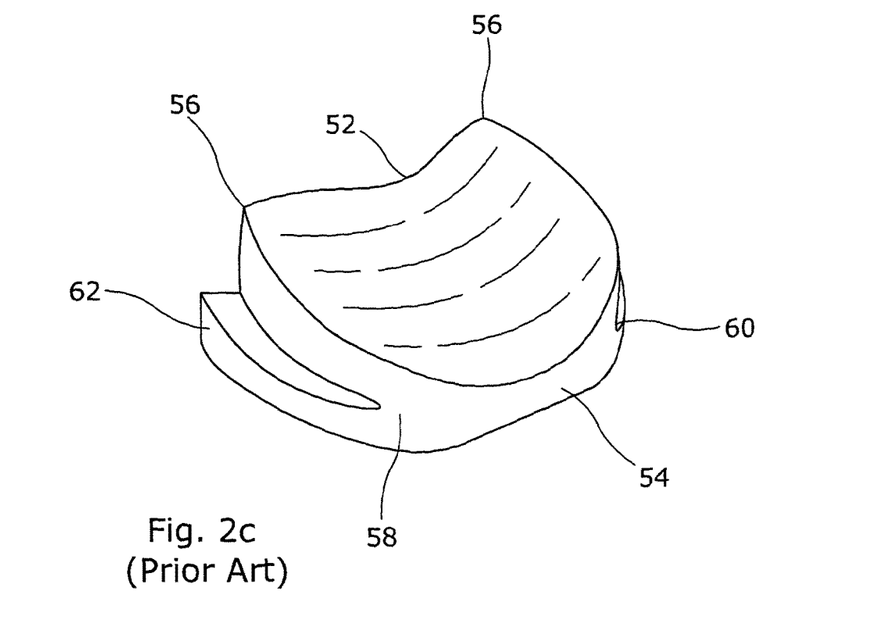
FIG. 2c shows schematically a prior art anatomically-shaped meniscal bearing.

FIG. 2c shows schematically an alternative design of meniscal bearing which has an anatomical shape. While the lateral side 52 and the medial side 54 are still generally parallel, the medial side 54 is shorter than the lateral side 52, and the medial corners 58 and 60 are of larger radii than those of lateral corners 56, which generally have equal radii. Anteromedial corner 58 may have a larger radius than posteromedial corner 60 to minimise bearing overhang in extension. The bearing also includes protrusions 62 extending from the lower portion of lateral corners 56 to the lower portion of medial corners 58 and 60. The anatomical shape reduces the likelihood of the bearing rotating on its flat base around a vertical axis, as the additional material comes into contact with the tibial wall.

Figure 3A:
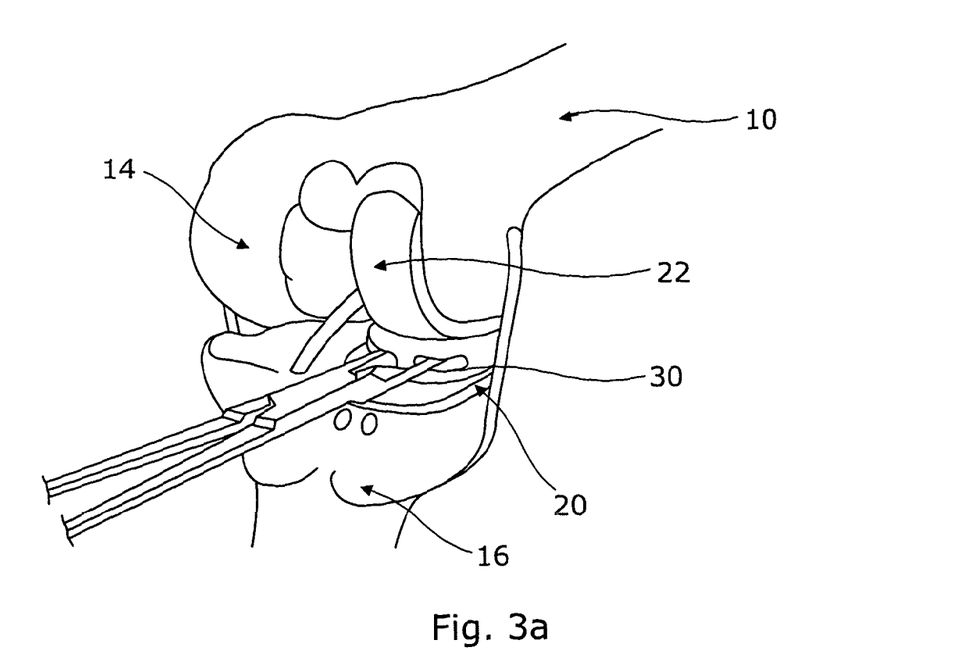
FIGS. 3a and 3b show a trial fitting of a trial meniscal bearing in a procedure to implant the unicondylar implant of FIG. 1.
Figure 3B:
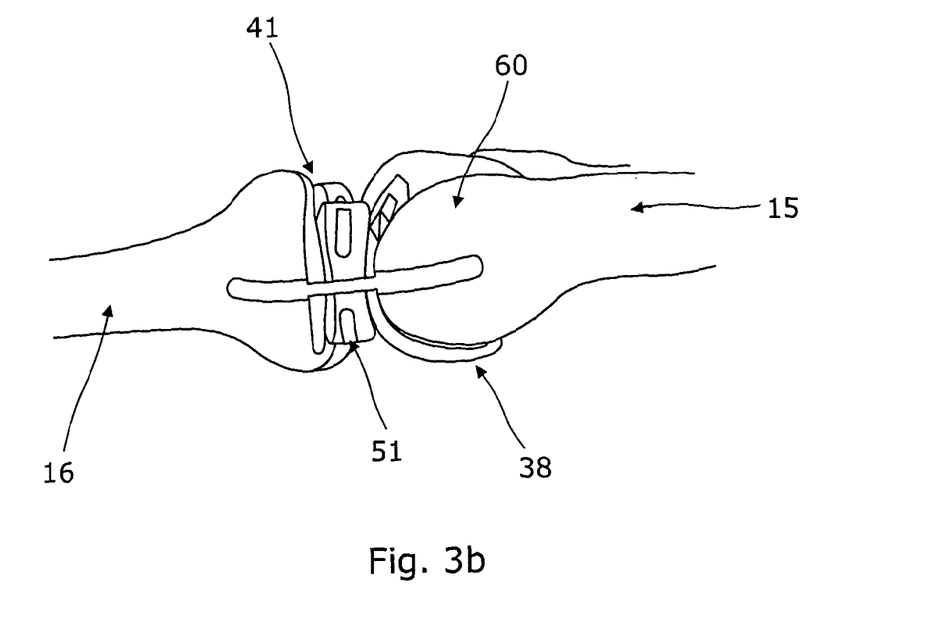

FIGS. 3*a* and 3*b* show the trial fitting of a trial meniscal bearing in a surgical operation. People come in different sizes, and prosthetic knee components come in different sizes, requiring femoral components of different radii & tibial components with different areas in plan view. After removing bone from a patient's damaged medial femoral condyle and fitting the femoral component 22 to it, and after removing bone from the damaged tibia and fitting the tibial component or plate 20 to it, there is a gap between the upper surface of the tibial plate and the domed surface of the femoral component. The meniscal bearing 24 is to fit in that gap.

The surgeon positions a patient's leg to a desired position, e.g. with the femur and tibia at about 90° to each other. The surgeon then selects a trial bearing 30, and inserts it into the gap to test the fit. The surgeon articulates the knee joint with the trial bearing in place to see if it will move properly, without problems, under a range of movement. There should still be a gap between the trial bearing and the other joint components, and that gap should remain more or less constant through the range of movement of the knee. The surgeon may choose to try a thicker bearing if he thinks that there is too much slack in the knee, or a thinner bearing if there is not enough slack.

The medial ligaments of the knee are strong and thick. It is hard to distract the joint (push the joint open) against their resistance. A surgeon often wants to ensure that the joint is not loose and so often tries to push into the gap the thickest meniscal bearing possible.

This can result in accidentally overstuffing the knee joint, which can cause problems later in use of the knee. The present invention helps to avoid such problems, especially with less experienced surgeons.

Up until now the entrapment of meniscal bearings has varied from about 3 mm for small patients, to about 4 mm for very large patients.

Figure 4:
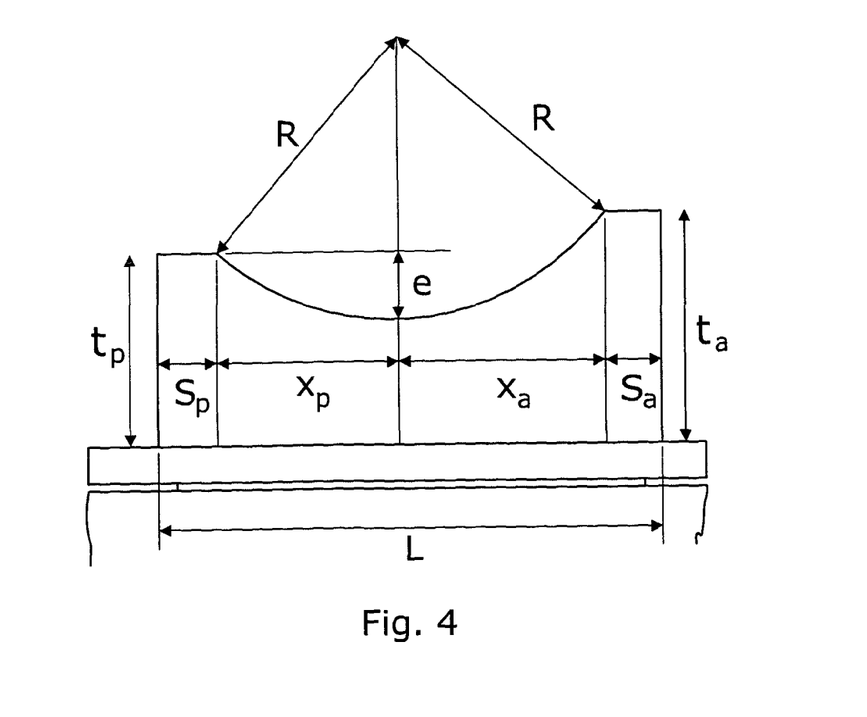
FIG. 4 shows a meniscal bearing and geometry for illustrating the relationship between radius of curvature R, and some geometrical features of the bearing.

Previous bearings used in unicondylar knee replacements, as shown in FIG. 4, have been constructed with a posterior lip or projecting edge having a bearing thickness of between 3 mm and 4 mm above the base of the bowl or dish of the meniscal bearing. The anterior lip or projecting edge of the bearing has had a thickness of around 5 mm above the base of the bowl. We have determined that, by reducing the entrapment to a range of about 3.2 mm for very small patients to about 3.8 mm for very large patients, or perhaps maintaining the entrapment of the meniscal bearing at around 3.5 mm for all sizes, it is more difficult to overstuff the joint in small patients, assisting in reducing post-operative pain to the patient, and it is easier to implant the correct thickness of bearing in large patients.

In our bearing we have realised that we may want consistent entrapment for any bearing thickness at its centre. That is to say, our bearing will sit with about the same level of slackness once it is in situ, and therefore we will avoid (or reduce the chance of) overstuffing. In the prior art the entrapment ($t_{max} - t_{min}$) train is normally about 3 mm to about 4 mm for the range of sizes of bearings. We would have consistent entrapment of about 3.5 mm, or a reduced entrapment range of 3.2 mm to 3.8 mm, increasing entrapment in the smaller sizes and decreasing it in the larger ones.

Table 1 below shows the relationship between $t_{max}$ and $t_{min}$ for some of the known prior art medial unicondylar meniscal bearings. In these cases, the anterior and posterior thicknesses are equal:

TABLE 1

(Extra Large Bearings)

| Size | $t_{max}$ (mm) ± 0.25 | $t_{min}$ (mm) ± 0.25 | $t_{max} - t_{min}$ | anterior-posterior length L (mm) ± 0.5 |
|---|---|---|---|---|
| 3XL | 7.54 | 3.5 | 4.04 | 39.5 |
| 4XL | 8.54 | 4.5 | 4.04 | 39.5 |
| 5XL | 9.54 | 5.5 | 4.04 | 39.5 |
| 6XL | 10.54 | 6.5 | 4.04 | 39.5 |
| 7XL | 11.54 | 7.5 | 4.04 | 39.5 |
| 8XL | 12.54 | 8.5 | 4.04 | 39.5 |
| 9XL | 13.54 | 9.5 | 4.04 | 39.5 |

In a large prior art bearing the sizes are shown in Table 2:

TABLE 2

| Size | $t_{max}$ (mm) ± 0.25 | $t_{min}$ (mm) ± 0.25 | $t_{max} - t_{min}$ | anterior-posterior length L (mm) ± 0.5 |
|---|---|---|---|---|
| 3L | 7.26 | 3.5 | 3.76 | 36.8 |
| 4L | 8.26 | 4.5 | 3.76 | 36.8 |
| 5L | 9.26 | 5.5 | 3.76 | 36.8 |
| 6L | 10.26 | 6.5 | 3.76 | 36.8 |
| 7L | 11.26 | 7.5 | 3.76 | 36.8 |
| 8L | 12.26 | 8.5 | 3.76 | 36.8 |
| 9L | 13.26 | 9.5 | 3.76 | 36.8 |

In a medium prior art bearing the sizes are as shown in Table 3:

TABLE 3

| Size | $t_{max}$ (mm) ± 0.25 | $t_{min}$ (mm) ± 0.25 | $t_{max} - t_{min}$ | anterior-posterior length L (mm) ± 0.5 |
|---|---|---|---|---|
| 3M | 7.0 | 3.5 | 3.5 | 34.2 |
| 4M | 8.0 | 4.5 | 3.5 | 34.2 |
| 5M | 9.0 | 5.5 | 3.5 | 34.2 |
| 6M | 10.0 | 6.5 | 3.5 | 34.2 |
| 7M | 11.0 | 7.5 | 3.5 | 34.2 |
| 8M | 12.0 | 8.5 | 3.5 | 34.2 |
| 9M | 13.0 | 9.5 | 3.5 | 34.2 |

In a prior art small bearing the sizes are as shown in Table 4:

TABLE 4

| Size | $t_{max}$ (mm) ± 0.25 | $t_{min}$ (mm) ± 0.25 | $t_{max} - t_{min}$ | anterior-posterior length L (mm) ± 0.5 |
|---|---|---|---|---|
| 3S | 6.73 | 3.5 | 3.23 | 31.6 |
| 4S | 7.73 | 4.5 | 3.23 | 31.6 |
| 5S | 8.73 | 5.5 | 3.23 | 31.6 |
| 6S | 9.73 | 6.5 | 3.23 | 31.6 |
| 7S | 10.73 | 7.5 | 3.23 | 31.6 |
| 8S | 11.73 | 8.5 | 3.23 | 31.6 |
| 9S | 12.73 | 9.5 | 3.23 | 31.6 |

In an extra small prior art bearing the sizes are as shown in Table 5:

TABLE 5

| Size | $t_{max}$ (mm) ± 0.25 | $t_{min}$ (mm) ± 0.25 | $t_{max} - t_{min}$ | anterior-posterior length L (mm) ± 0.5 |
|---|---|---|---|---|
| 3XS | 6.48 | 3.5 | 2.98 | 29.2 |
| 4XS | 7.48 | 4.5 | 2.98 | 29.2 |
| 5XS | 8.48 | 5.5 | 2.98 | 29.2 |
| 6XS | 9.48 | 6.5 | 2.98 | 29.2 |
| 7XS | 10.48 | 7.5 | 2.98 | 29.2 |
| 8XS | 11.48 | 8.5 | 2.98 | 29.2 |
| 9XS | 12.48 | 9.5 | 2.98 | 29.2 |

Figure 2D:
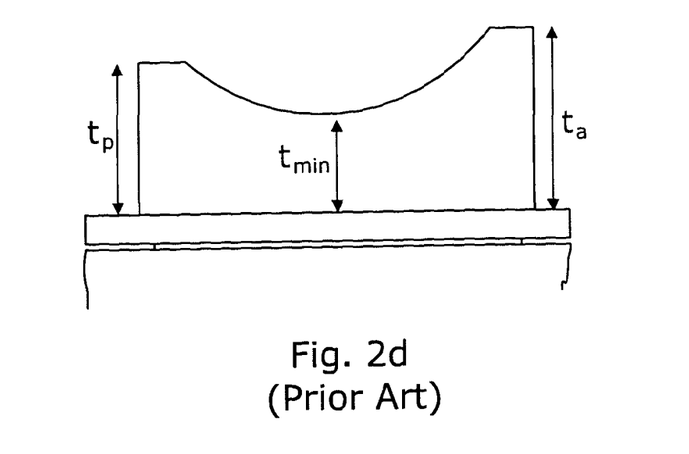
FIG. 2d shows schematically a prior art meniscal bearing.

FIG. 2d shows a prior art meniscal bearing for a medial unicondylar arthroplasty. The height $t_p$ is lower than the height $t_a$: that is to say the bearing has a thicker dimension at its anterior end than at its posterior end. As discussed in relation to Tables 1 to 5, the entrapment at its posterior end ranges from about 4 mm for the extra large bearing range to 3 mm in the extra small size range.

We have discovered that there may be advantages in having the entrapment proportionally larger in smaller patients and proportionally smaller in larger patients.

It will be appreciated that smaller people need smaller prosthetic components, including smaller bearings. It is well known to have several sizes of femoral, tibial and bearing components. Each patient is adjudged by a medical practitioner (possibly the surgeon in a pre-operative review) to be extra small, small, medium, large, or extra large. At the time of surgery the surgeon is provided with a kit of trial components that are "extra small", "small", "medium", "large", or "extra large". In each kit there is a range of different sizes of trial tibial components, a range of different sizes of trial femoral components and a range of different sizes of trial meniscal bearings.

It will be appreciated that the surgeon is in the operating theatre with the patient and, e.g., 6 or 7 trial tibial components, 6 or 7 trial femoral components, and 6 or 7 trial sets of meniscal bearings. As he selects/tries out the trial components he selects the correct size to be used. The implantable prosthetic components corresponding to the trial size are then ordered and delivered, typically from a store outside of the operating theatre, and the implantable components are fitted into place.

The surgeon may first remove a slice of bone from the medial tibial plateau, exposing a plane surface. He selects the correct size of tibial template, a plate with flat upper and lower surfaces, which best fits the exposed surface. He removes a sliver of bone from the posterior femoral condyle. He confirms that the femoral and tibial components are correctly placed so that the minimum gap between the components in extension is the same as that in flexion. The surgeon then has to select the correct thickness of bearing.

After the surgeon has fitted the femoral component (having first tried selected trial components and having selected the size that best suits the patient after femoral bone has been removed), and after fitting the tibial component (having first tried selected trial components to find the size of tibial component that best suits the patient after tibial bone has been removed), the surgeon has to select the correct thickness of bearing.

The surgeon has a range of, for example, large left leg medial trial meniscal bearings to choose from, each with an associated cylindrical gap gauge. He inserts a gap gauge into the gap between the tibial and femoral components and flexes and extends the knee. He progressively removes bone from the damaged distal femoral condyle until the minimum gap between the components in extension is the same as that in flexion. If the gap gauge seems too loose he takes it out and inserts a thicker gap gauge. He confirms his choice of bearing thickness by inserting the corresponding trial bearing. Traditionally, surgeons are afraid of having the joint too loose and so they tend to choose the thickest size bearing they can force in. This can result in overstuffing.

We have realised that in the prior art, the lower/thinner posterior end of the bearing also means that the entrapment to the rear of the bearing is lower than the entrapment to the front of the bearing (see FIG. 2d).

In our invention, the entrapment at the rear may be larger than in the prior art for small and extra small bearings, and smaller than in the prior art for large and extra large bearings. The entrapment at the rear may be around 3.5 mm for all bearing sizes in our invention.

By entrapment, we may mean the difference in thickness between the lowermost portion of the dished surface of the bearing and whichever is the thinnest/shallowest of the anterior or posterior end regions of the bearing if they have different thicknesses.

The anterior-posterior length of the bearing varies between sizes of bearing (e.g. between extra small, small, medium, large and extra large).

For a part spherical bearing surface, FIG. 4 illustrates that the entrapment is related to the radius of curvature R of the part spherical surface and the horizontal distance $x_p$ from the posterior extreme of the curved surface to the lower extreme of the curved surface.

The length of the bearing L is determined by the size of the patient's bone structure—it should not be too long. The distance $s_a$ and $s_p$ from the anterior and posterior extremities of the bearing respectively to the start of the part-spherical bearing surface are shown in FIG. 4. In some embodiments $s_a = s_p$, but in others it does not.

As shown in FIG. 4, by Pythagoras' Theorem, $$e = R - \sqrt{R^2 - x_p^2}$$

or expressed another way:

$$x_p = \sqrt{2Re - e^2}$$

where e=the entrapment, R=the radius of curvature, and x the length of the chord from the vertical centre line to the posterior of the curved bearing surface.

If $s_a = s_{p=about}$ 4 mm, e=3.5 mm and the anterior-posterior bearings are as in Tables 1 to 5 of the prior art, then this gives:

| Size of Bearing | R | $x_p$ |
|---|---|---|
| Extra large | 27.92 | 13.53 |
| Large | 26.08 | 13.05 |
| Medium | 24.25 | 12.55 |
| Small | 22.35 | 12.01 |
| Extra small | 20.7 | 11.5 |

We have appreciated that for some of our embodiments, instead of, as in the prior art, having the posterior end of the bearing less thick than the anterior end—making it easier to push in, we should have the posterior end not substantially thinner, or no thinner, than the anterior end (and in some embodiments the same thickness).

This will, for the same anterior thickness, make the bearing harder to push in. This reduces the chance of overstuffing—any given level of force to push the test bearing results in the choice of a final bearing that is a little thinner at the anterior end than was previously the case, and so for the same sized (length anterior-posterior and radius of curvature R) bearing we have a similar entrapment, and, compared to the prior art, a thinner (as measured at the depth of the spherical socket) bearing, but a thicker bearing, as measured at the posterior end, that is harder to push in.

In some embodiments, our bearing is symmetric about a coronal plane and also about a sagittal central plane. This means that our bearing is no longer handed—we no longer need a left knee medial bearing and a different, handed, right knee medial bearing. Similarly, our test bearings need then not be handed—they could be symmetric. This can reduce parts inventory. They can also be inserted either way around. They do not have different anterior and posterior profiles and heights: they are the same.

In another embodiment, our bearing is implanted by holding it against the anterior surface of the femoral component and sliding it round into the gap between the femoral and tibial components. This may require smaller distraction of the femoral component and a smaller force required for distraction for a given entrapment. This is true for a smaller measurement of $s_p$ from the posterior extremity of the bearing to the start of the part-spherical bearing surface.

Figure 5:
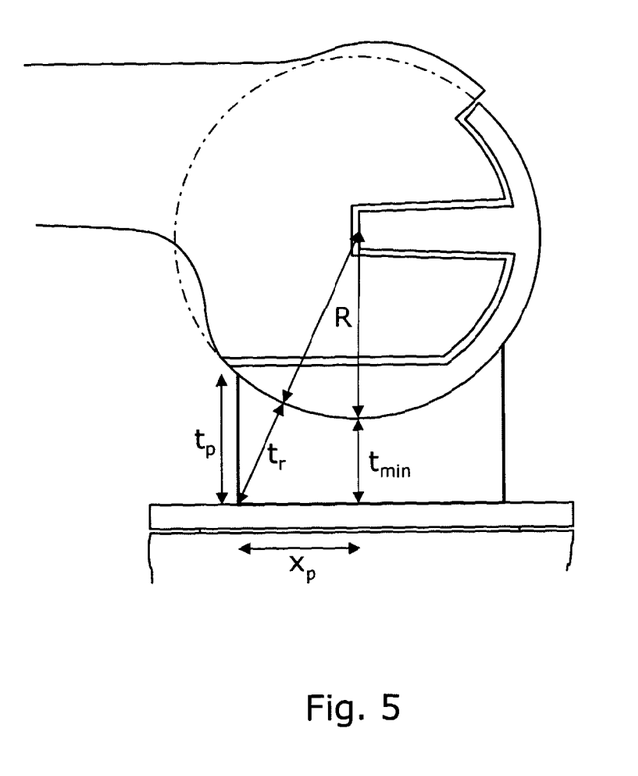
FIG. 5 shows schematically a unicondylar arthroplasty.

FIG. 5 shows a unicondylar knee replacement including a bearing with negligible values of $s_a$ and $s_p$.

The vertical thickness of the posterior extremity of the bearing $t_p$ is given by $$t_p = t_{min} + R - \sqrt{R^2 - x_p^2}$$

R is the external radius of the femoral component and the radius of the concavity of the upper surface of the bearing and $x_p$ is the posterior half length of the concavity of the upper surface of the bearing.

$t_{min}$ is minimum thickness of the meniscal bearing. For a given $t_{min}+R$, $t_p$ can be increased by increasing $x_p$. The maximum radial thickness of the posterior end of the bearing $t_r$ is given by $$t_r = \sqrt{(R+t_{min})^2 + x_p^2} - R$$

For negligible values of $s_a$, the vertical thickness of the posterior extremity $t_p$ will always be larger than the maximum radial thickness $t_r$. Therefore less distraction and force will be required when implanting the bearing along the femoral component, as shown in FIG. 6b.

Figures 6A, 6B:
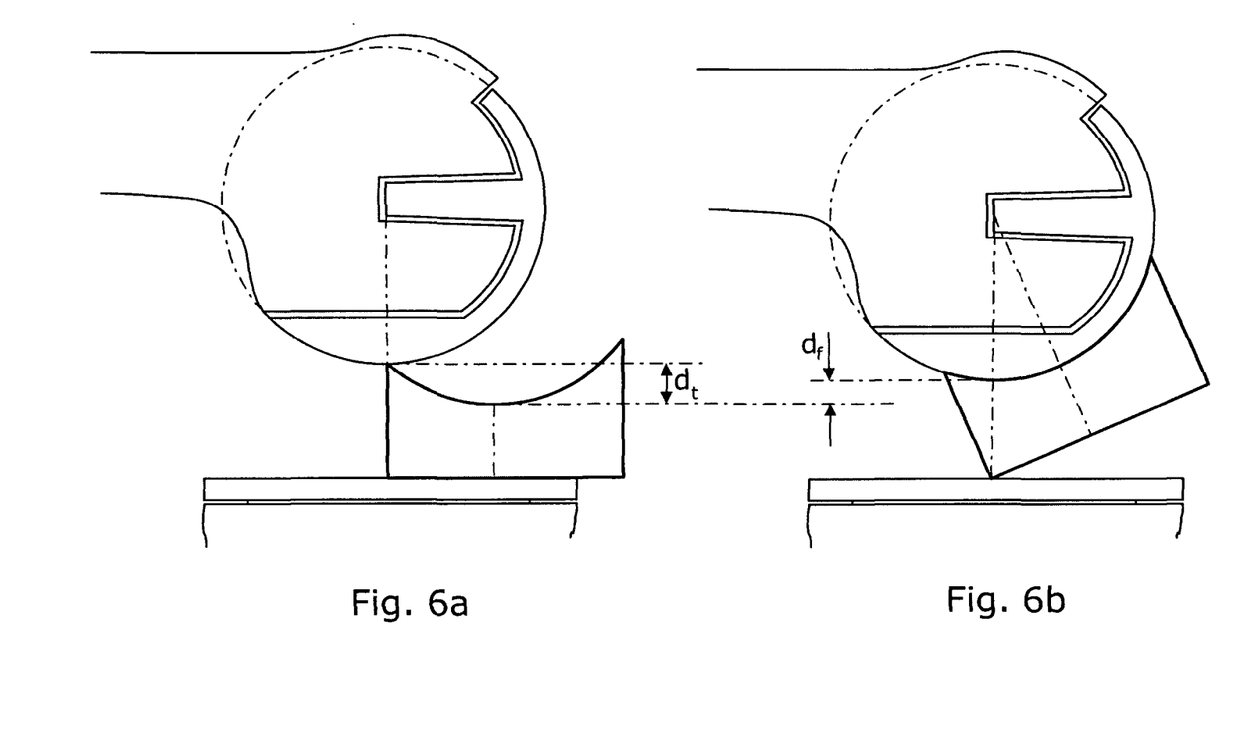
FIG. 6a shows a meniscal bearing implantation along the tibial component.
FIG. 6b shows a meniscal bearing implantation along the femoral component.

The distraction $d_f$ required for implantation of the bearing along the femoral component, as shown in FIG. 6b, is as follows:

$$d_f = t_r, t_{min} = \sqrt{(R+t_{min})^2 + x_p^2} - R - t_{min}$$

From this, it can be deduced that, as the minimum thickness of the bearing $t_{min}$ is increased, the distraction, and therefore the force, required for implantation along the femur decreases.

Figure 7:
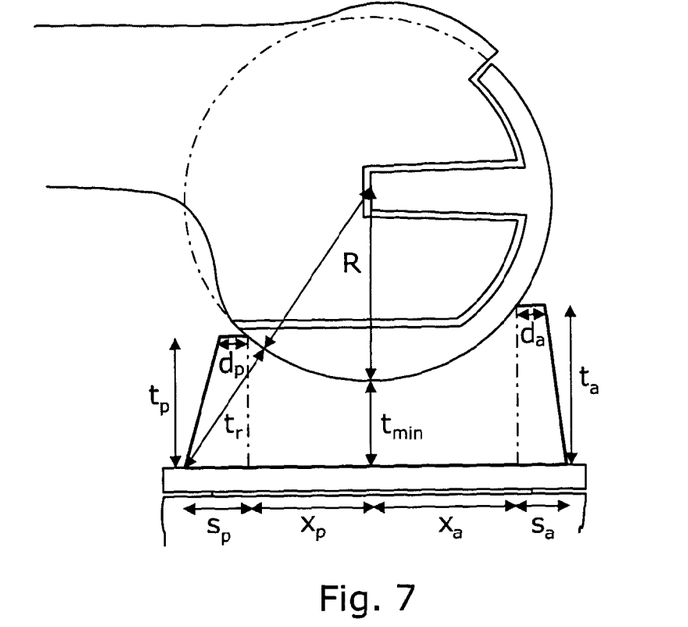
FIG. 7 shows schematically another embodiment of a unicondylar arthroplasty.

In some embodiments, the distraction and force required to insert the bearing horizontally along the tibia is equal to the distraction required to insert the bearing along the femur. Using the geometry in FIG. 7, it can be shown that the vertical thickness of the posterior extremity will be equal to the radial thickness when $s_p$ is calculated as follows:

For $t_p = t_r$, $$s_p = \sqrt{\left(t_{min} + 2R - \sqrt{R^2 - x_p^2}\right)^2 - (t_{min} + R)^2} - x_p$$

| Size of Bearing | $x_p$ | R | $s_p$ |
|---|---|---|---|
| Extra large | 15.5 | 32 | 1.9 |
| Large | 14 | 26.5 | 2.1 |
| Medium | 13 | 23 | 2.3 |
| Small | 11.5 | 18.5 | 2.5 |
| Extra small | 10.5 | 16 | 2.6 |

In some embodiments, the distraction and force required to insert the bearing horizontally along the tibia are larger than the distraction and force required to insert the bearing along the femur. This will be the case when $s_p$ is larger than the corresponding value given above.

In some embodiments, the distraction and force required to insert the bearing horizontally along the tibia is larger than the force and distraction required to insert the bearing along the femur. This will be the case when $s_p$ is smaller than the corresponding value given above.

Figure 8:
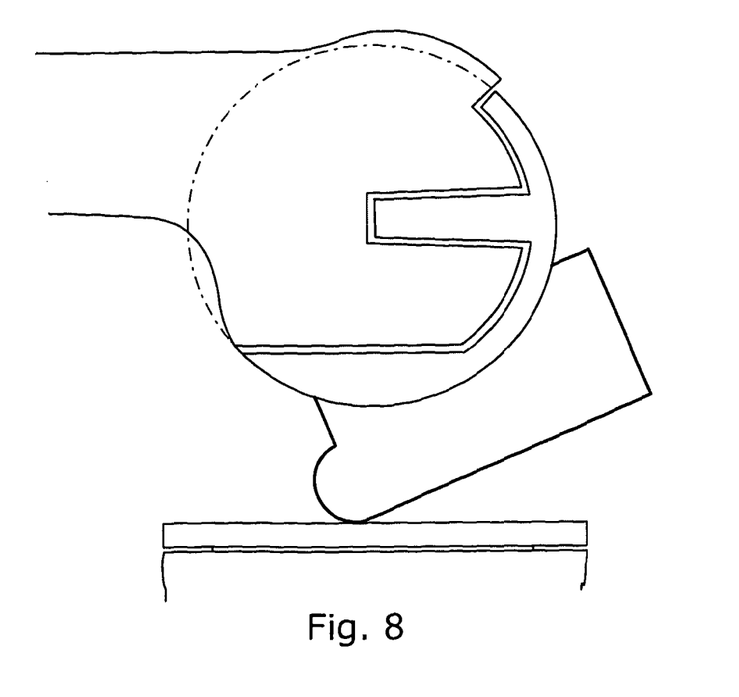
FIG. 8 shows another embodiment of a meniscal bearing implantation along the femoral component.

In order to increase the posterior half-length of the bearing while not significantly increasing the minimum posterior radial thickness of the bearing, material can be added to the posterior vertical surface in a semi-cylindrical shape, as shown in FIG. 8, to form a protrusion.

The invention claimed is:

1. A system of parts for use in unicondylar meniscal bearing knee replacement, the system comprising;
    a plurality of meniscal bearings ranging in size including an extra small bearing having an anterior-posterior length of 29.2±0.5 mm, a small bearing, a medium bearing, a large bearing, and an extra large bearing having an anterior-posterior length of 39.5±0.5 mm, each meniscal bearing comprising a body defining a dished first bearing surface on one side thereof and a second surface on an opposing side thereof;
    wherein each meniscal bearing has an entrapment defined as the difference in thickness between the smaller of the maximum thicknesses between the first and second surfaces at an anterior and posterior end and the minimum thickness between the first and second surfaces, the entrapment of each meniscal bearing being between 3.2 mm at least for the extra small bearing and 3.8 mm at most for the extra large bearing.

2. The system of claim 1, wherein the entrapments of the meniscal bearings are all approximately the same.

3. The system of claim 2, wherein the entrapments of the meniscal bearings are all approximately 3.5 mm.

4. The system of claim 1, wherein the meniscal bearings have a plurality of different lengths.

5. The system of claim 1, wherein the length of at least one of the meniscal bearings is at least 39 mm.

6. The system of claim 1, wherein the length of at least one of the meniscal bearings is less than 31.6 mm.

7. The system of claim 1, wherein the meniscal bearings have a plurality of different minimum thicknesses between the first and second surfaces.

8. The system of claim 1, wherein the meniscal bearings of a given length have approximately the same entrapment.

9. The system of claim 1, wherein the meniscal bearings are trial bearings for use in fitting a prosthesis or implantable bearings for use with the prosthesis.

10. The system of claim 1, further comprising;
a set of trial bearings and a set of implantable bearings, each implantable bearing corresponding to one of the trial bearings.

11. The system of claim 10, wherein the correspondence between the trial and implantable bearings is such that, after a thickest grade trial bearing insertable into a gap between tibial and femoral components of a patient's knee is identified, the implantable bearing one grade thinner than the thickest grade trial bearing is selected for implantation.

12. The system of claim 1, wherein at least one of the meniscal bearings is symmetrical about either or both of a coronal plane and a sagittal plane.

13. The system of claim 1, further comprising;
at least one femoral prosthetic component having a spherical articular surface with a radius of curvature, the first surfaces of the meniscal bearings having the same radius of curvature.

14. The system of claim 1, further comprising;
at least one tibial prosthetic component.

15. The system of claim 1, wherein at least one of the meniscal bearings comprises at least one protrusion at a posterior end thereof, an anterior end thereof, or both ends thereof.

16. The system of claim 15, wherein each protrusion is of even depth along the end on which it is located.

17. The system of claim 15, wherein each protrusion has a reduced depth at its upper end compared with its lower end, giving a sloped edge.

\* \* \* \* \*